United States Patent [19]

Hieftje et al.

[11] Patent Number: 4,642,778
[45] Date of Patent: Feb. 10, 1987

[54] METHOD AND DEVICE FOR SPECTRAL RECONSTRUCTION

[75] Inventors: Gary M. Hieftje; David H. Honigs, both of Bloomington, Ind.

[73] Assignee: Indiana University Foundation, Bloomington, Ind.

[21] Appl. No.: 585,575

[22] Filed: Mar. 2, 1984

[51] Int. Cl.$^4$ .............................................. G06F 15/46
[52] U.S. Cl. .................................. 364/498; 364/497; 364/716
[58] Field of Search ............... 364/498, 497, 484, 485, 364/576, 572, 716, 726, 724; 343/55 A; 73/659; 324/310, 312; 382/17; 356/300, 303, 402, 425; 250/226; 340/722

[56] References Cited

U.S. PATENT DOCUMENTS

| | | | |
|---|---|---|---|
| 3,961,172 | 6/1976 | Hutcheon | 364/819 |
| 4,097,801 | 6/1978 | Freeman et al. | 368/120 |
| 4,100,378 | 7/1978 | Claasen et al. | 364/728 X |
| 4,266,277 | 5/1981 | Issenmann | 364/498 |
| 4,286,327 | 8/1981 | Rosenthal et al. | 364/497 X |
| 4,493,048 | 1/1985 | Kung et al. | 364/728 X |

OTHER PUBLICATIONS

Honigs, D. E., Hieftje, G. M., Hirschfeld, T., "A New Method for Obtaining Individual Component Spectra from Those Complex Mixtures", *Applied Spectroscopy*, vol. 38, No. 3, 1984, pp. 317-322.
Dormey et al. "Extraction of Mass Spectra Free of Background and Neighboring Component Contributions from Gas Chromatography/Mass Spectrometry Data", *Analytical Chemistry*, vol. 48, No. 9, Aug. 1976, pp. 1368-1375.
W. R. Hruschka and K. H. Norris, Appl. Spectrosc. 36,261 (1982).
P. C. Williams, K. H. Norris, R. L. Johnson, K. Standing, R. Friconi, D. MacAffrey, and R. Mercier, Cereal Foods World 23,544 (1978).

*Primary Examiner*—Errol A. Krass
*Assistant Examiner*—Joseph L. Dixon
*Attorney, Agent, or Firm*—Kirkland & Ellis

[57] ABSTRACT

A method is presented for spectral reconstruction which comprises first obtaining component concentrations of a series of mixtures, which component concentrations constitute a set of reference values. The spectral value of each member of that series of mixtures is measured at a first wavelength, which spectral value possesses contribution from individual components in the mixture, whose individual contribution is unknown. The spectral values for the series of mixtures are then mathematically cross-correlated with the component concentrations in said series of mixtures, at the first wavelength, thereby obtaining the spectral contribution for said components at that first wavelength. The spectral value of each member of that series of mixtures is measured at the second wavelength, which spectral values are then cross-correlated with component concentrations in the series of mixtures thereby obtaining the spectral contribution for said components at the second wavelength. This operation is repeated for a series of wavelengths until the spectrum of the desired component in the mixture is reconstructed. Devices are presented which implement the methods for spectral reconstruction of the present invention.

19 Claims, 8 Drawing Figures

METHOD AND DEVICE FOR SPECTRAL RECONSTRUCTION

Background of the Invention

1. Field of the Invention

The present invention relates to a novel method and device for reconstruction of spectra from spectral information obtained from complex mixtures.

2. Description of the Prior Art

Spectroscopic methods may be used to measure spectral values of a series of samples of known composition at several discrete wavelengths in order to predict the concentration of one or more chemical species in an "unknown" sample. Present methods require the use of a set of samples of known composition whose spectra are employed as a "training set" of data comprising a set of wavelengths and weighting coefficients for a multilinear regression algorithm. The "training set" data then may be applied to a spectrum of a sample of unknown composition to determine the percent composition of the component or components in the sample. This spectroscopic technique can be applied to many methods of spectroscopy and has been applied successfully to samples in which almost complete spectral overlap obscures individual bands; where no band is interference-free; and where background fluctuations far exceed spectral changes caused by the compositional changes of interest.

Methods are also known for extracting a spectrum from complex mixtures. Perhaps the most widely used of these techniques is termed spectral stripping or curve-fitting. Spectral stripping requires that the spectrum of each of the pure components of a mixture be known and that the spectrum of the mixture be a linear combination of the pure components. Thus, for spectral stripping the components must not exhibit complicating interactions which affect the structure of the resultant spectrum. Such complicating interactions include changes in symmetry, chemisorption, physisorption and especially hydrogen bonding -- interactions which prevent the spectra of most mixtures from being linear combinations of their components. In near-infrared reflectance analysis, samples such as wheat are analyzed for their moisture and protein content. Such spectra exhibit complex intermolecular interactions between the components of the sample.

The ratio method is a second method which can be used to generate reconstructed spectra of components of a sample. This technique involves generating a ratio from spectra of several samples containing the same components in varying proportion. The resultant ratio is used to locate regions of the spectrum where one component dominates. Indeed, the use of the ratio method requires that each component must dominate the spectrum in at least one "window" region and is thus limited to relatively simple mixtures. However, in some spectroscopic regions (including the near-infrared region of the spectrum) most transitions are very broad and overlapping, which makes resolving components in the spectra of even simple mixtures nearly impossible.

A third method for reconstructing spectra is factor analysis. The eigenvectors of factor analysis provide spectral information on the discrete contributors present, and their eigenvalues are related to component concentrations. However, these eigenvectors represent only independently varying entities, and are not necessarily associated with specified (or indeed any) components. Even where such an association exists, its detection requires very good spectral differentiation, considerable expertise, or auxiliary chemical data. In the latter case, factor analysis can actually be complemented by an abridged form of spectral reconstruction. When the component sought contains independently varying constituents, that component will itself never appear as a factor, and its individual constituents might easily lie below the noise and be indetectable.

It is thus an object of the present invention to provide a spectral reconstruction technique that does not require the spectrum of the pure component and that provides reproducible spectra even when components exhibit complex intermolecular interactions.

It is yet a further object of the present invention to reconstruct spectra from complex mixtures in which a significant degree of overlap occurs in the region of the spectrum being studied.

It is yet a further object of the present invention to provide methods and devices to produce spectra corresponding precisely to the component of interest, even when the latter is ill-defined chemically.

It is yet another object of the present invention to provide a rapid, convenient method for reconstructing near-infrared component spectra. Based on a mathematical cross-correlation procedure, the technique requires only a set of near-infrared spectra of samples in which the concentration of the component of interest is known. Thus, the method of the present invention avoids the difficulties of, and errors inherent in, the use of spectra of pure components.

SUMMARY OF THE INVENTION

In one aspect, the present invention comprises a method for spectral reconstruction which comprises first obtaining component concentrations in a series of mixtures, which component concentrations constitute a set of reference values. The spectral value of each member of that series of mixtures is measured at a first wavelength, which spectral value possesses unknown contribution from individual components in the mixture. The spectral values for the series of mixtures are then cross-correlated with the component concentrations in the series of mixtures at the first wavelength, thereby obtaining the spectral contribution for the component at that first wavelength. This operation may be repeated for a series of wavelengths. The cross-correlation operation is then applied to the series of spectral values for that series of wavelengths until the spectrum of the component in the mixture is reconstructed.

In its device aspect this invention comprises means for obtaining the concentrations of at least one component in a series of mixtures of components, the component concentrations constituting a set of reference values; spectrometer means for obtaining spectral values for each mixture in the series of mixtures, the spectral values possessing unknown contribution from components in the mixtures; data storage means for storing reference values and spectral values; data input means for supplying reference values to the data storage means; spectral reconstructor means for cross-correlating the reference values and spectral values thereby providing a spectral contribution for the one component; and data output means for outputting the spectral contribution for the one component.

DETAILED DESCRIPTION OF THE INVENTION

Figure 1:
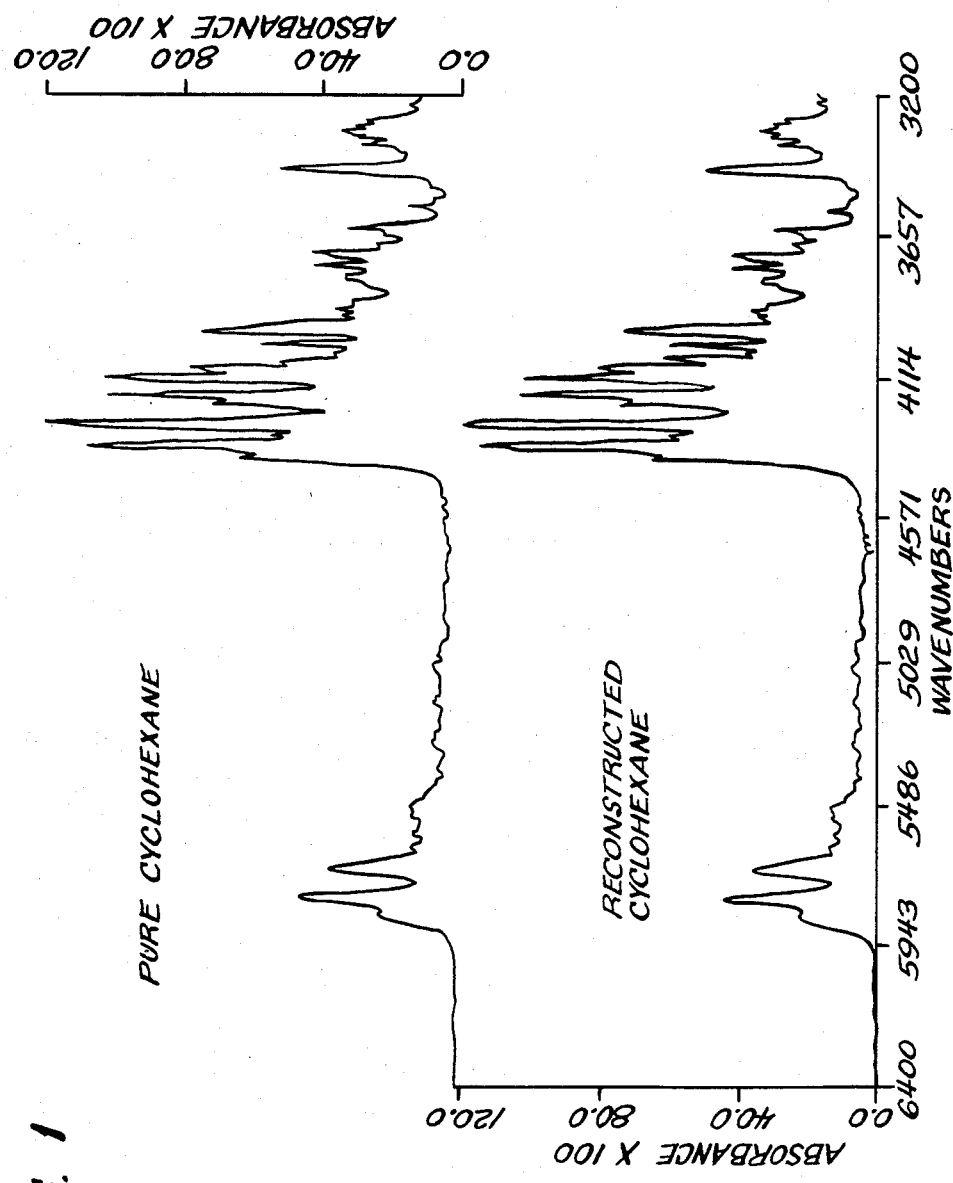
FIG. 1 is the spectrum of pure cyclohexane and a spectrum reconstructed from several mixtures of cyclohexane, benzene, iso-octane and n-heptane. The scales of these spectra have not been normalized.

The present invention provides a method and device for obtaining spectral information from a sample whose component concentrations are known or determined (the "reference values") and for generating a reconstructed spectrum of the component or components of interest. Utilizing the methods of the present invention, the common procedure of determining the composition of unknowns through use of reference spectra of the components is reversed. Instead "reference spectra" are generated based on information concerning the quantitative composition of the sample.

From the correlation between known concentration values and the spectral information, usually absorbance or reflectance information, of each sample at individual wavelengths, the spectrum of the individual components can be displayed. Such reconstructed spectra reflect the presence of the components in a particular sample and can be used to deduce the nature of matrix interactions.

Near-infrared reflectance analysis (NIRA) is an analytical spectroscopic technique that utilizes the near-infrared diffuse reflectance of a series of samples of known composition at several wavelengths to determine the concentration of components in an "unknown" sample. To obtain the most complete information from NIRA it would be desirable to have available the near-infrared spectra of the individual components of the sample. Unfortunately, pure components for spectral analysis are often unavailable. In addition, the spectra obtained for pure components often differ significantly from the spectra of mixtures containing that component, expecially when the spectrum of the component is influenced by the other components and its surroundings in the sample, e.g., samples with strong matrix effects.

Any method may be used for measuring component concentration of the series of samples to generate the reference values. For example, in the examples described below for hydrocarbon mixtures, the series of reference values were generated by knowing the weight of introduced component hydrocarbons. Other methods which could have been used include the use of gas chromatography or other methods, including methods involving wet chemistry. Thus, there is no limitation in the present invention on the methods for obtaining the reference values comprising the component compositions of the series of samples.

While the examples of the present invention specifically describe the use of near-infrared reflectance spectroscopy for measuring the spectral information for the series of samples, it should be understood that substantially any spectral method may be used in which the signal produced thereby is proportional to the concentration of the component in the sample. Examples include mid-infrared spectroscopy, far-infrared spectroscopy, ultraviolet spectroscopy, visible spectroscopy, mass spectrometry, nuclear magnetic resonance spectroscopy, microwave spectroscopy, electron spin resonance spectroscopy, chromatography techniques, flourescence spectroscopy, and the like.

In addition, no particular near-infrared reflectance spectrometer is contemplated by the present invention. Thus, grating, Fourier transform and filter instruments are contemplated for use in the present invention.

1. Methods for Spectral Reconstruction

The methods and devices of the present invention for spectral reconstruction involve mathematical cross-correlation. The methods of the present invention can be directly applied to reconstruct a spectrum of a desired component in a complex mixture. A sequence of spectral values is obtained for a series of mixtures at a particular wavelength in samples of known concentration. Thus, concentrations of the desired component in that same series of mixtures must be known. These concentrations constitute a set of reference values. Cross-correlation of the spectral values and reference values retains that portion of the signal which contains spectral information attributable to the desired component. The methods of the present invention further eliminates noise, which can be spectral information or background from any other source. When the methods of the present invention are repeated at a number of wavelengths over a selected range, the spectrum of the desired component over that range of wavelengths is obtained.

In its most general form the cross-correlation function can be written as the summation:

$$C_{ab}(d) = \frac{1}{n} \sum_{x=1}^{n} a(x)b(x \pm d) \quad d = 0, 1, 2 \ldots n - 1 \quad (1)$$

where n is the number of samples, x is the sample index and d is the displacement from the current x index. $C_{ab}(d)$ is the value of the cross-correlation function between signals a(x) and b(x) at the displacement d.

In the application of Eq. 1 to NIRA, a(x) is the absorbance (or its reflectance analog) of the xth sample at a specific wavelengt and b(x) is the concentration of the desired component in the xth sample. In the absence of noise or other absorbing components in the sample set, the value of $C_{ab}(d)$ at d=0 depends only on the absorbance and concentration of the desired component and all values of the cross-correlation function at d≠0 are zero. Although it would appear trivial to extract the desired spectrum from repeated applications of Eq. 1 at various wavelengths, experimental noise, interference from other sample constituents, and a limited number of samples cause the zero and non-zero d terms of the cross-correlation function to contain small undesired contributions. To overcome these errors, the average of the non-zero d terms is subtracted from the value of $C_{ab}(d)$ at $d=0$. This correction is shown in Eq. 2.

$$C_{ab} = \frac{1}{n} \sum_{x=1}^{n} a(x) b(x) - \frac{1}{n(n-1)} \sum_{d=1}^{n-1} \sum_{x=1}^{n} a(x) b(x \pm d) \quad (2)$$

Eq. 2 can be rewritten as:

$$C_{ab} = \frac{1}{n} \sum_{x=1}^{n} [a(x) - \bar{a}] [b(x) - \bar{b}] \quad (3)$$

wherein $\bar{a}$ is the average absorbance of all samples at a given wavelength and $\bar{b}$ is the average fractional concentration of a given component. When this calculation is repeated for a number of wavelengths and plotted against wavelength, the resulting spectrum shows the correlation between the sample absorbance and the concentration of the desired component.

Eq. 3 should be normalized so the resulting reconstructed spectrum appears in convenient, concentration-independent units. This is performed by dividing Eq. 3 by the variance of $b(x)$, as shown in Eq. 4.

$$C'_{ab} = \frac{\sum_{x=1}^{n} [a(x) - \bar{a}] [b(x) - \bar{b}]}{\sum_{x=1}^{n} [b(x) - \bar{b}]^2} \quad (4)$$

In NIRA, $C'_{ab}$ in Eq. 4 has units of absorbance per unit concentration. The application of Eq. 4 has been found to be useful in the analysis of non-interacting solutes, in which the concentration of each solute has no effect on the concentrations of other solute contained therein.

However, some samples, especially solids, are comprised of mixtures where the fractional concentration of each species influences the concentrations of others, because the fractional concentrations must sum to unity. In such a situation Eq. 4 contains a correlation attributable to the desired component, as well as negative correlation caused by the effect of the concentration of that component on the concentrations of all other constituents.

The negative correlation in Eq. 4 can be eliminated by scaling Eq. 4 by the true average concentration of "other" species and adding to the product the average sample absorbance at that wavelength. This correction is shown in Eq. 5, an expression which is valid as long as the concentration [b(x)] is expressed as a dimensionless fraction.

$$C''_{ab} = \left[ \frac{\sum_{x=1}^{n} [a(x) - \bar{a}] [b(x) - \bar{b}]}{\sum_{x=1}^{n} [b(x) - \bar{b}]^2} \right] (1 - \bar{b}) + \bar{a} \quad (5)$$

By applying Eq. 4 or Eq. 5 to spectral information obtained over a series of wavelengths, the spectrum of the component may be reconstructed. The correlation methods of the present invention rely on linearity of the underlying function and, thus, Eq. 5 applies only in the absence of nonlinear effects such as physical or chemical nonadditivity, e.g., as Beer's law deviations. This limitation is not severe, because NIRA and many other spectroscopic techniques mentioned above are based on linear-response assumptions.

One advantage of the methods of the present invention is that each reconstructed spectrum will receive only that noise which is phase coherent with its analytical guiding values. All other noise appears as a residual when component spectra are subtracted from the original data.

Spectral reconstruction requires more samples than does curve-fitting, and accurate reference chemical values which are not necessary for ratio deconvolution or factor analysis. However, NIRA applications also require several samples and accurate reference chemical values. This compatibility makes spectral reconstruction particularly well suited to elucidate the spectral details of NIRA samples.

2. Devices for Spectral Reconstruction

Figure 8:
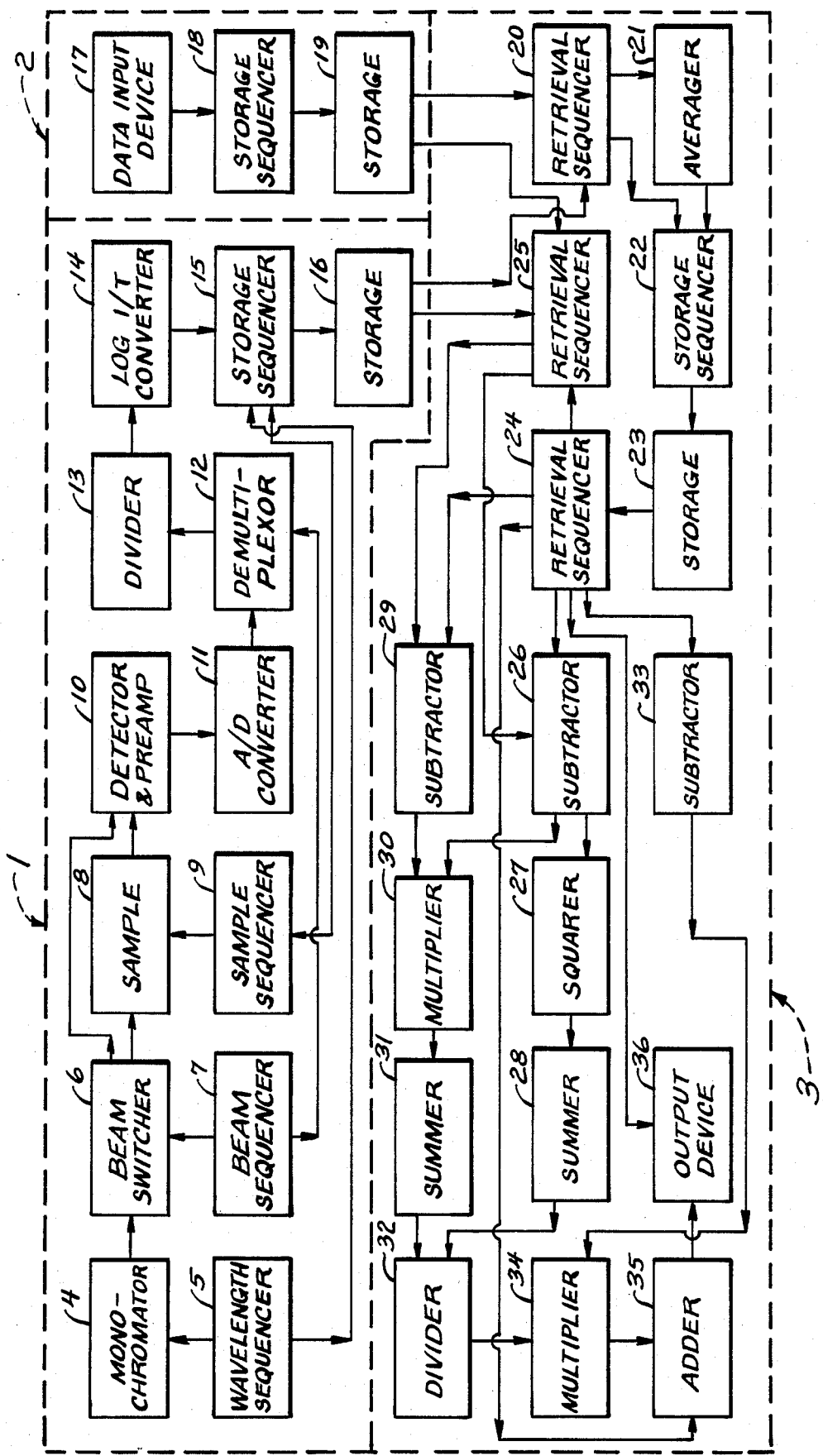
FIG. 8 is an embodiment of a device which utilizes the spectral reconstruction methods of the present invention.

A schematic diagram of a preferred embodiment of a device which implements the process of spectral reconstruction is shown in FIG. 8. This system comprises three principal subsystems: a spectrometer 1 capable of measuring the spectral values of a series of samples 8 at a series of wavelengths and storing the spectral values for processing; a data input means 2 allowing input and storage of reference data for the component of the samples for which a reconstructed spectrum is desired; and the spectral reconstructor 3 which utilizes the spectral data for a series of samples and the reference data for the component of interest, mathematically cross-correlates the data and generates a spectrum therefor.

The spectrometer configuration shown in FIG. 8 is designed for use in near-infrared reflectance spectral reconstruction methods and can be substantially any commercially available spectrometer. Described herein is a scanning nearinfrared spectrometer such as a Cary Model 14. Commercial Fourier transform instruments such as a Digilab Model 15C can also be used. The monochromator 4 contains an optical energy source, such as a tungsten-halogen lamp and means to select a narrow band of wavelengths, such as optical filters or a diffraction grating. The output of the monochromator is a narrow beam of monochromatic light. The wavelength input to the monochromator is controlled by the wavelength sequencer 5, which in a preferred embodiment consists of a stepper motor electronically programmed to scan the wavelength over a preselected range thereby providing the wavelength information for the spectrum of a sample. Beam switcher 6 is controlled by beam sequencer 7 and alternately directs the output energy to sample 8 or to detector 10. Samples are sequentially introduced into the beam by sample sequencer 9, which may be manually or automatically operated. Sample number (x) is stored on digital storage device 16 for identification of the data for each sample. The monochromatic beam directed to the sample, is either transmitted through the sample or reflected from the sample whereby the sample absorbs some energy, thereby producing an energy from the sample 8 containing the desired spectral information. The detector 10 converts the optical energies of the sample and reference beams to electrical signals. Said signals are converted to digital form by the analog to digital converter 11 and separated by the demultiplexer 12 using timing information from the beam sequencer 7. The ratio of intensities of the sample signal to the reference signal which is the transmittance or reflectance of the sample, is formed by divider 13. This may be any conventional digital divider circuit. Transmittance or reflectance is converted to absorbance ($a(x)$) by a conventional digital log 1/T converter 14. When performed at a series of wavelengths, the absorbances (a(x)) together with the sample number, and the wavelengths are placed in a digital storage device 16, by the storage sequencer 15. Digital storage device 16 is preferably a magnetic disc or tape to provide means for permanent data storage.

The data input means 2 is a conventional data input subsystem consisting of a data input device 17, preferably a keyboard and display device, a storage sequencer 18 which places the reference data values and sample number in digital storage device 19. Preferably, the reference data values for the component of interest, b(x), are stored associated with the absorbance data, (a(x)), on digital storage device 19.

The spectral reconstructor 3, performs the spectral reconstruction process whereby the absorbance data (a(x)) of the sample and the reference data (b(x)) are processed to produce the reconstructed spectrum of the desired component. The spectral reconstructor can be substantially any minicomputer and can be a commercial DEC PDP11-34 or Data General Nova. The first step of the process is the sequential retrieval of the b(x) values and the a(x) values by retrieval sequencer 20. The retrieval sequencer retrieves b(x) and a(x) information for all the samples in sequence and passes the data to the averager 21 together with the total number of samples (n). The averager 21 adds the data for all the samples together in a digital register and then divides the sum by the total number of samples using conventional digital techniques. The average of the b(x) values ($\bar{b}$) and the average of the a(x) values for each wavelength ($\bar{a}$) are then stored by storage sequencer 22 in storage 23, which preferably is conventional digital random access memory, using the reference data and wavelength information from the retrieval sequencer 20 to identify the data from the averager 21.

The process continues with the wavelength retrieval sequencer 24 selecting a first wavelength, and retrieving $\bar{b}$ and $\bar{a}$ from storage 23. Simultaneously, the wavelength retrieval sequencer 25, using the information from the retrieval sequencer 24, selects a first x and retrieves b(x) from digital storage device 19 and a(x) from digital storage device 16.

The values of b(x) and $\bar{b}$ are passed from the retrieval sequencers 24 and 25 to subtractor 26, a conventional digital subtractor, which produces the difference (b(x)−$\bar{b}$), thence to squarer 27, a conventional digital multiplier which produces (b(x)−$\bar{b}$)$^2$, which is then passed to summer 28. The associated values of a(x) and $\bar{a}$ are passed from retrieval sequencers 24 and 25 to subtractor 29, which is another conventional digital subtractor, producing (a(x)−$\bar{a}$), which is then passed to multiplier 30. The output of subtractor 26, (b(x)−$\bar{b}$) is also passed to multiplier 30, which produces the product (a(x)−$\bar{a}$)(b(x)−$\bar{b}$), which is then passed to summer 31.

The wavelength retrieval sequencer 25 sequentially increments the sample number x to retrieve the a(x) and b(x) data for each sample in turn thereby sequentially providing the summers 28 and 31 with processed data for each sample at each wavelength. Summer 28, which is a conventional adder with an accumulator register, provides the summation from one to n of all (b(x)−$\bar{b}$)$^2$ at the conclusion of the sequence of sample data and summer 31 produces the summation from one to n of all (a(x)−$\bar{a}$)(b(x)−$\bar{b}$) in similar fashion. The outputs of summers 28 and 31 are passed to digital divider 32 which divides the output of summer 31 by that of summer 28 by conventional digital techniques, producing the result of Eq. 4.

The value of $\bar{b}$ from the wavelength retrieval sequencer 24 is passed to subtractor 33 where the difference (1-$\bar{b}$) is formed by conventional digital techniques. The output of divider 32 is multiplied by the output of subtractor 3 in multiplier 34, another conventional digital multiplier and then passed to adder 35. Here, the value of $\bar{a}$ from the wavelength retrieval sequencer 24 is added to the output of multiplier 34 by conventional digital techniques to provide C″$_{ab}$ at one wavelength of the desired reconstructed spectrum of component x, where C″$_{ab}$ is defined in Eq. 5. The output of adder 35 together with the value of the wavelength retrieval sequencer 24 is then passed to output device 36, which may be a data storage device, display printer, or plotter, to produce one point of the reconstructed spectrum.

The process is continued by causing wavelength retrieval sequencer 24 to increment to the next wavelength and repeating the above cycle of processing to produce the next point of the reconstructed spectrum. The cycle is repeated until all desired wavelengths have been processed and the complete reconstructed spectrum of the desired component has been obtained.

Example I

Spectral Reconstruction from Hydrocarbon Mixtures

Figure 2:
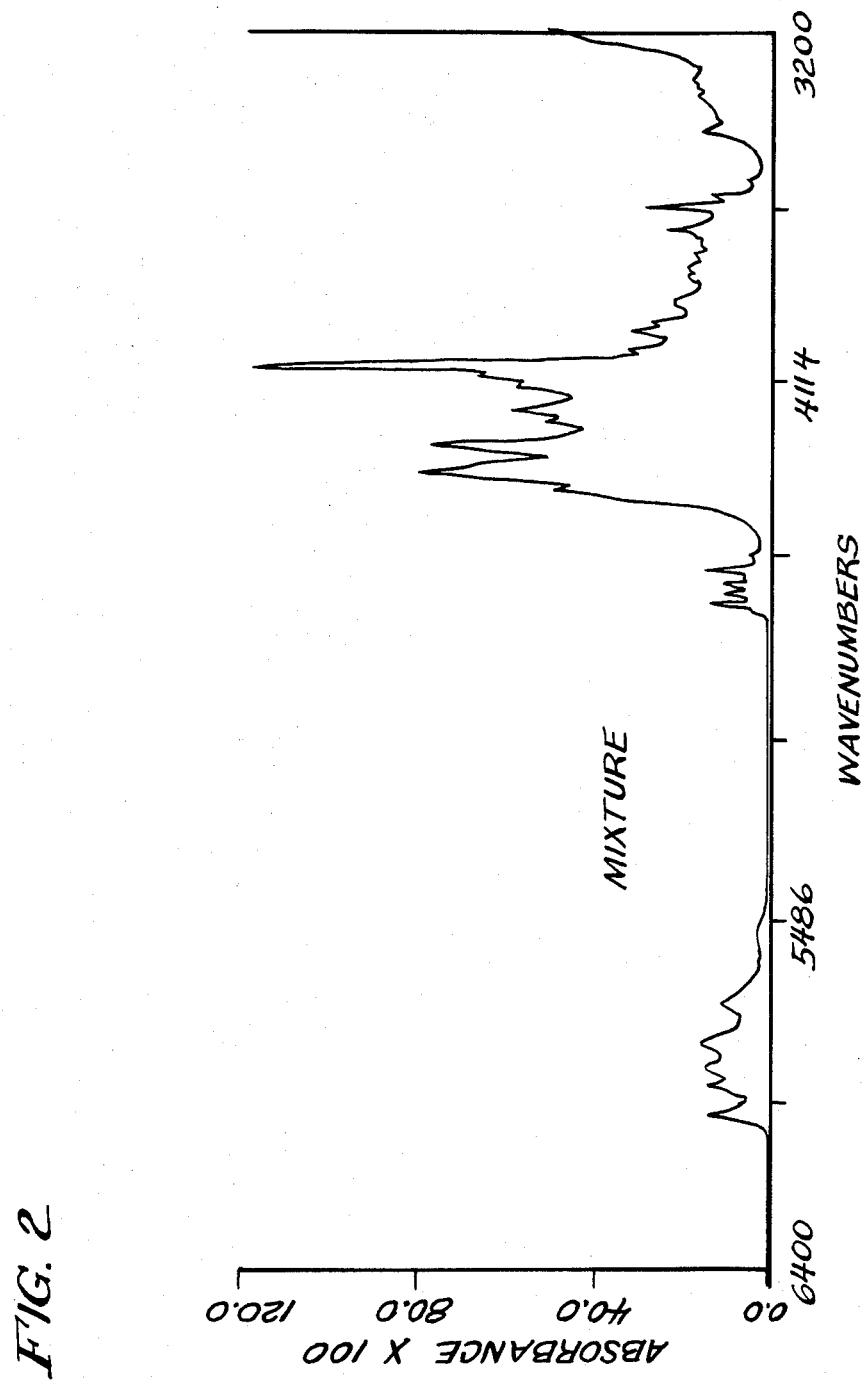
FIG. 2 is a spectrum of a typical hydrocarbon mixture composed of 12% benzene, 43% iso-octane, 26% cyclohexane and 20% n-heptane.
Figure 3:
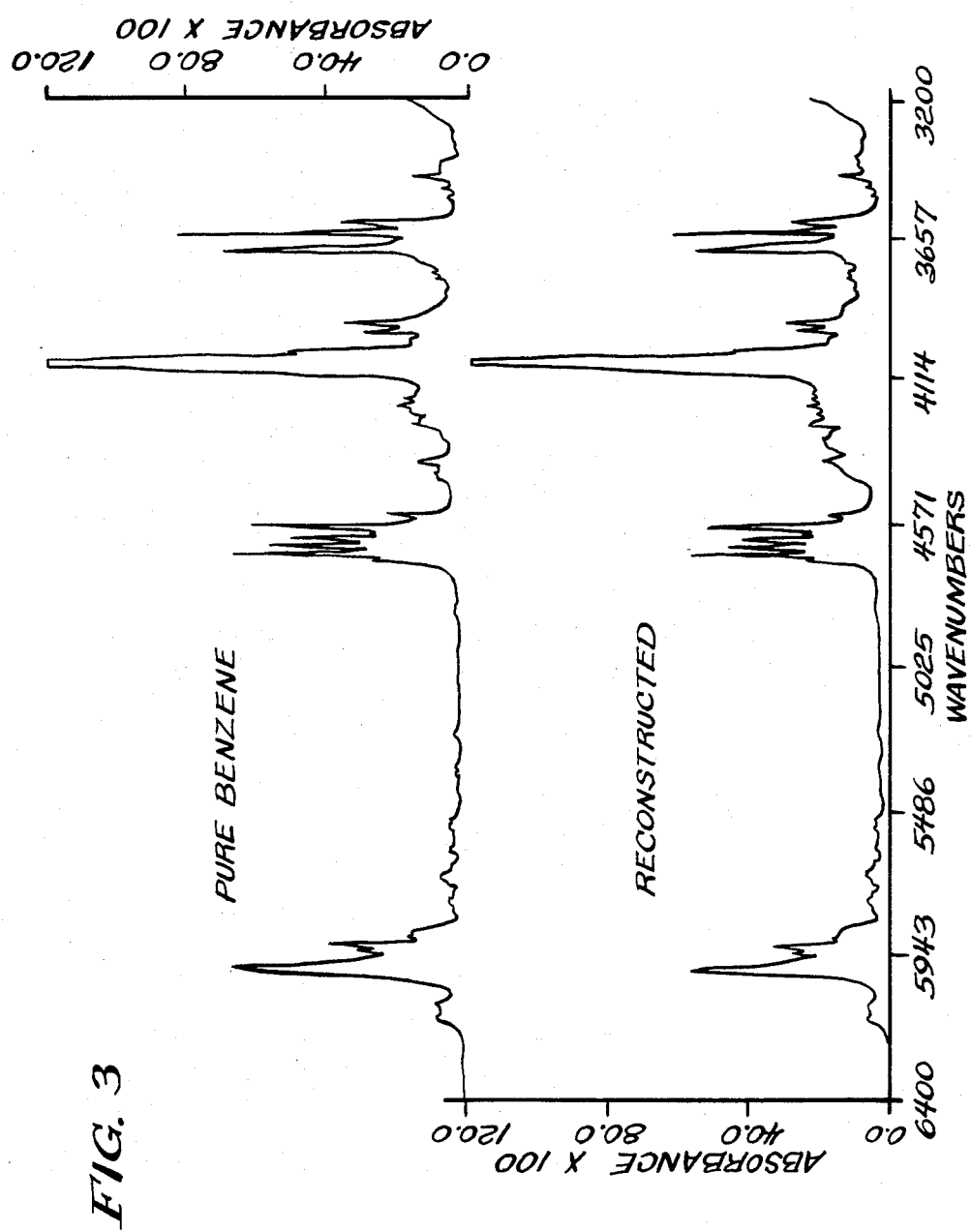
FIG. 3 is a spectrum of pure benzene and a spectrum of benzene reconstructed from hydrocarbon mixtures.
Figure 4:
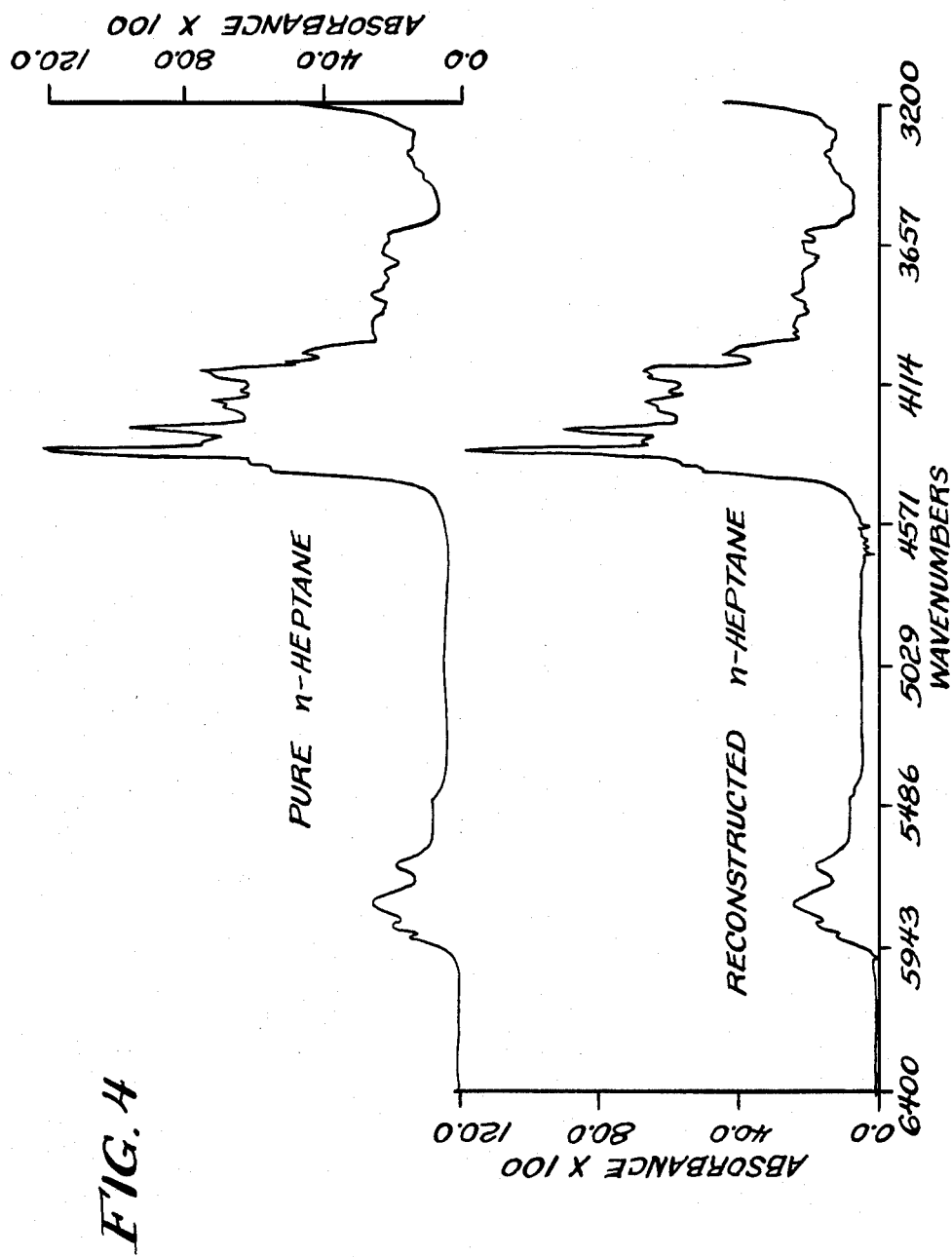
FIG. 4 is a spectrum of pure n-heptane and a spectrum reconstructed fro hydrocarbon mixtures.
Figure 5:
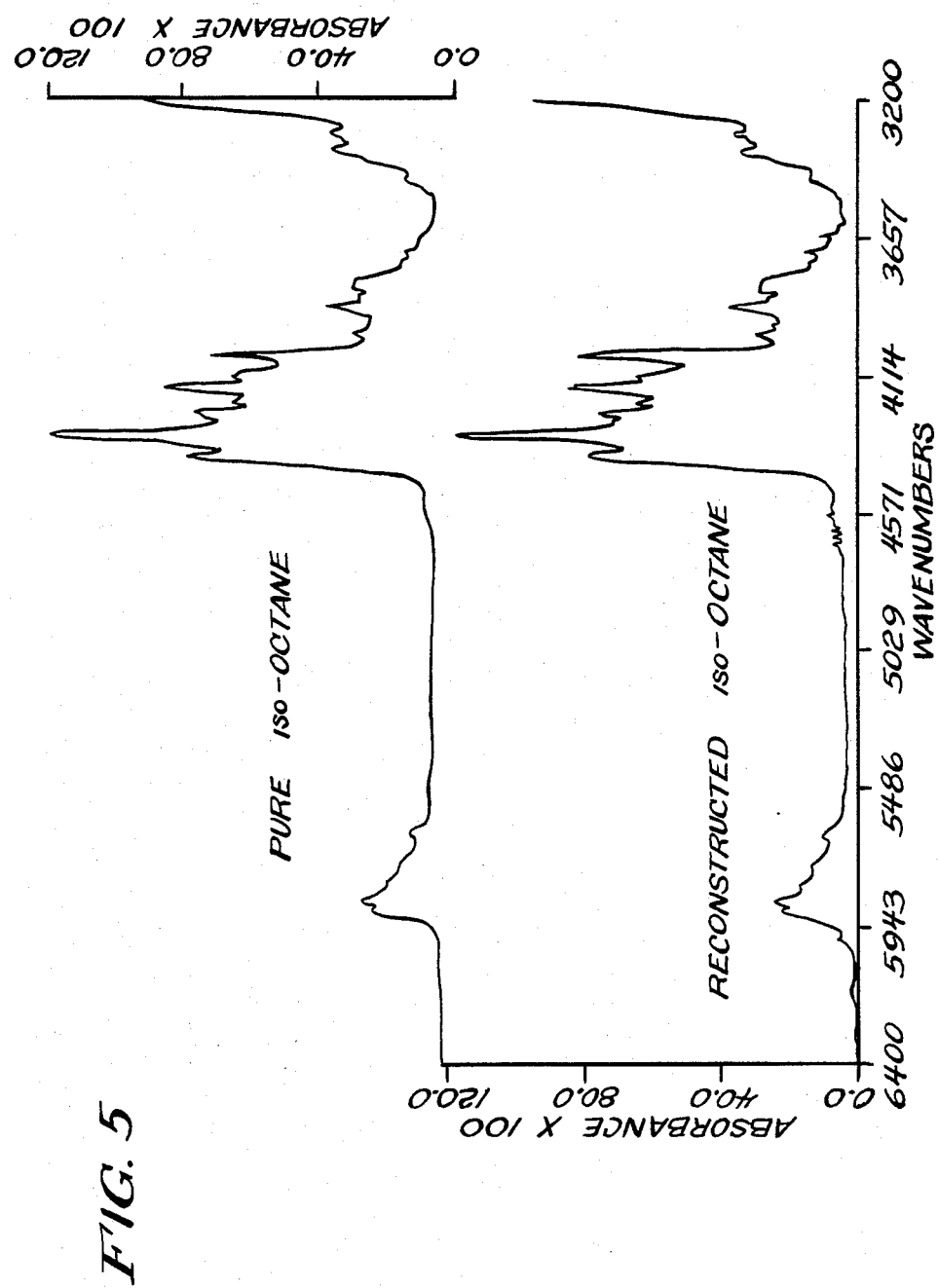
FIG. 5 is a spectrum of pure iso-octane and a spectrum reconstructed from hydrocarbon mixtures.

Spectra of hydrocarbons were reconstructed from hydrocarbon mixtures prepared as follows. Reagent-grade benzene and cyclohexane, and spectranalyzed iso-octane and n-heptane were combined in varying proportions to create 97 standard hydrocarbon solutions. These solutions ranged from 3% to 100% concentration for each hydrocarbon. To minimize error, each of the four hydrocarbons was rapidly introduced and weighed by difference into a gas-tight vial. The error in each standard concentration is estimated at b 0.05%. Infrared spectra were recorded by a Fourier-transform spectrometer having a silicon beam splitter, a PbSe detector operated at 300° C., and a CaF$_2$ flow-through cell. The instrumental resolution was nominally 4 cm$^{-1}$ and boxcar apodization was employed. Reconstructed spectra were calculated according to Eq. 5. The reconstructed spectrum of cyclohexane obtained from hydrocarbon mixtures is shown in FIG. 1 along with a spectrum of pure cyclohexane obtained during an independent run. A spectrum of a typical hydrocarbon mixture (benzene, cyclohexane, iso-octane and n-heptane) is shown in FIG. 2. A comparison of the reconstructed spectrum and that of the mixture shows that even intense background features in the mixture do not "bleed" through the reconstruction process and affect its accuracy. Moreover, the identity of the vertical scales in FIG. 1 shows the fidelity of the reconstructed spectrum; both the band location and amplitude are the same as found in the spectrum of the pure compound. FIGS. 3–5 show the pure and reconstructed spectra of the remaining components in the hydrocarbon mixtures. Each of these compounds shows the same high degree of similarity between the pure and reconstructed spectra as found for cyclohexane. This similarity is not surprising; the compounds used to create hydrocarbon mixtures are known to exhibit few intermolecular interactions.

Although the reconstructed spectra of FIG. 1 and FIGS. 3–5 appear very similar to those of the pure compounds, the spectra of the pure components were not used or required to generate the reconstructed spectra. Similarly, the spectral reconstruction technique is able to produce spectr of individual mixture components even when the pure components cannot be obtained. An example of this capability can be found in the determination of moisture in wheat flour.

Example II

Spectral Reconstruction of Protein and Moisture in Wheat

Spectra were reconstructed for protein and moisture in wheat samples as follows. A set of 50 near-infrared diffusereflectance spectra of wheat-flour samples was obtained from USDA, Beltsville, MD. Each of these spectra is comprised of 125 reflectance values obtained over the spectral range 1000–2587.2 nm in increments of 12.8 nm. The reported instrumental bandpass was 7 nm. Each of the four samples was characterized for protein by 32 separate Kjeldahl measurements. A spectrum of distilled water was obtained from a 0.5 mm transmission cell with CaF$_2$ windows using the Fourier transform spectrometer as described in Example I. Reconstructed spectra were calculated according to Eq. 5.

Figure 6:
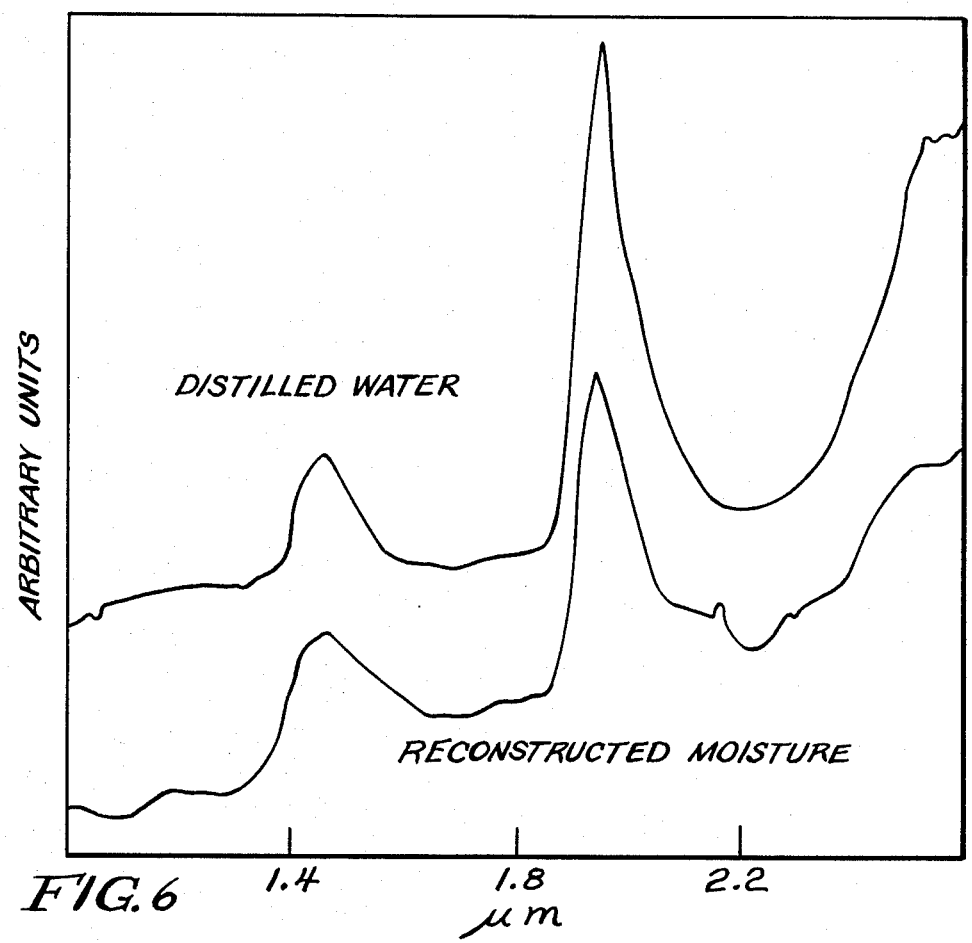
FIG. 6 is a spectrum of pure water and a spectrum of wheat moisture reconstructed from wheat samples.

An absorbance spectrum of pure water and the reconstructed spectrum of moisture in wheat flour, shown in FIG. 6, are noticeably different. In particular, the bands at 1450 nm and 1950 nm appear broader in the reconstructed spectrum than in the spectrum of pure water. This change is indicative of variations in hydrogen bonding caused by the protein matrix. Additionally, two small peaks at 2150 nm and 2300 nm appear in the reconstructed spectrum. These absorptions are due to protein and oil respectively and show that the moisture, protein and oil content of wheat are either biologically or chemically correlated.

FIG. 6 shows a spectrum of reconstructed moisture in wheat which reasonably approximates pure water, but shows the spectral deviations of moisture in wheat described by Hruschka et al., Applied Spectroscopy 36,261 (1982).

Spectral reconstruction is able to extract from a sample set the composite spectrum of constituents responsible for sensory characteristics such as flavor or taste. A similar capability is the spectral reconstruction of Kjeldahl determined protein and "as is" protein.

Figure 7:
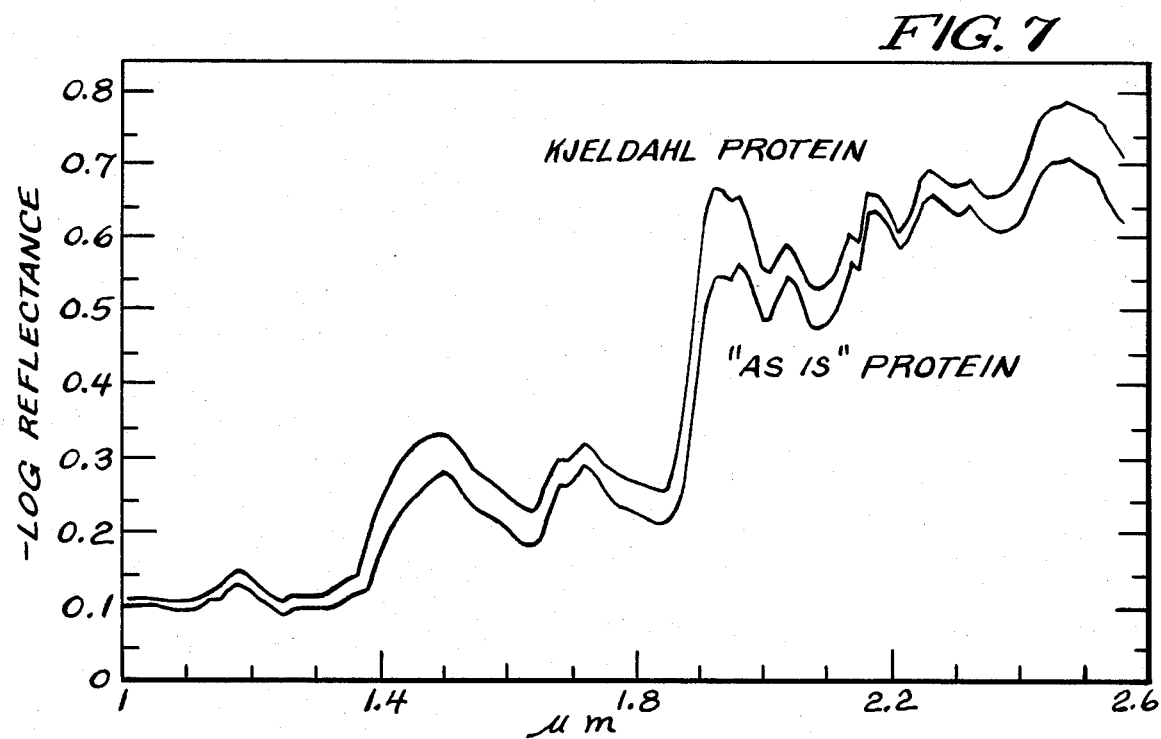
FIG. 7 is a reconstructed spectrum of protein wherein the protein content was determined in wheat samples by the Kjeldahl method and by the "as is" method.

"As is" protein has been defined as protein which has been determined by the Kjeldahl method but which has been adjusted for the moisture content of the sample. The reconstructed spectra of protein determined by the Kjeldahl technique and by the "as is" measurement are reproduced in FIG. 7. These spectra are plotted on the same scale and are not offset. From FIG. 7, both measurements generate the same spectrum, suggesting that both measure essentially the same chemical species. However, there are some slight differences in the relative intensities of several of the peaks. For example, the moisture absorption band at 1950 nm is slightly smaller in the "as is" protein spectrum than in the Kjeldahl spectrum, indicating the "as is" measurement of protein reduces but does eliminate interferences from moisture.

While the above examples describe certain methods of the present invention they are not to be construed as limitations on the present invention. As one skilled in the art would recognize, many modifications may be made in the methods and devices of the present invention which fall within the spirit and scope of the present invention.

What is claimed:

1. A method for spectral reconstruction comprising the steps of:
    (a) obtaining the concentrations of a first component in a series of mixtures of components, the concentrations of the first component constituting a set of reference values;
    (b) measuring spectral values for each mixture in the series of mixtures at a series of wavelengths;
    (c) cross-correlating, at a first wavelength, the spectral values for each mixture in the series of mixtures with the corresponding reference values for the one component at the first wavelength to obtain the spectral contribution for the one component at the first wavelength;
    (d) outputting the spectral contribution for the one component at the first wavelength;
    (e) repeating steps c and d at wavelengths other than the first wavelength, until the spectrum of the one component is obtained.

2. A method as claimed in claim 1 wherein the cross-correlating step comprises calculating:

$$C'_{ab} = \frac{\sum_{x=1}^{n} [a(x) - \bar{a}][b(x) - \bar{b}]}{\sum_{x=1}^{n} [b(x) - \bar{b}]^2} \quad (4)$$

wherein n is the number of mixtures in the series of mixtures, x is the mixture index, a(x) is the spectral value of the mixture x at the first wavelength, b(x) is the reference value of the first component in the mixture x, $\bar{a}$ is the average spectral value of all mixtures in the series of mixtures at a first wavelength, $\bar{b}$ is the average fractional concentration of the first component in the series of mixtures, and $C'_{ab}$ is the value of the cross-correlation function between a(x) and b(x).

3. A method as claimed in claim 2 wherein the spectrum is a near-infrared reflectance spectrum.

4. A method as claimed in claim 1 wherein the cross-correlating step comprises calculating:

$$C''_{ab} = \left[\frac{\sum_{x=1}^{n} [a(x) - \bar{a}][b(x) - \bar{b}]}{\sum_{x=1}^{n} [b(x) - \bar{b}]^2}\right](1 - \bar{b}) + \bar{a} \quad (5)$$

wherein n is the number of mixtures in the series of mixtures, x is the mixture index, a(x) is the spectral value of the mixture x at the first wavelength, b(x) is the reference value of the first component in the mixture x, $\bar{a}$ is the average spectral value of all mixtures in the series of mixtures at a first wavelength, $\bar{b}$ is the average fractional concentration of the first component in the series of mixtures, and $C''_{ab}$ is the value of the cross-correlation function between a(x) and b(x).

5. A method as claimed in claim 4 wherein the spectrum is a near-infrared relectance spectrum.

6. A method as claimed in claim 1 wherein the spectrum is a near-infrared reflectance spectrum.

7. A device for spectral reconstruction:
    (a) means for obtaining the concentrations of a first component in a series of mixtures of components, the concentrations of the first component constituting a set of reference values;

(b) spectrometer means for obtaining spectral values for each mixture in the series of mixtures;

(c) data storage means for storing the reference values and spectral values;

(d) data input means for supplying the reference values and spectral values to the data storage means;

(e) spectral reconstructor means for cross-correlating the corresponding reference values and spectral values stored in the data storage means, thereby providing a spectral contribution for the one component;

(f) data output means for outputting the spectral contribution for the one component.

8. A device as claimed in claim 7 wherein the means for spectral reconstruction cross-correlates the reference values and spectral values according to the equation:

$$C'_{ab} = \frac{\sum_{x=1}^{n} [a(x) - \bar{a}][b(x) - \bar{b}]}{\sum_{x=1}^{n} [b(x) - \bar{b}]^2} \quad (4)$$

wherein n is the number of mixtures in the series of mixtures, x is the mixture index, a(x) is the spectral value of the mixture x at the first wavelength, b(x) is the reference value of the first component in the mixture x, $\bar{a}$ is the average spectral value of all mixtures in the series of mixtures at a first wavelength, $\bar{b}$ is the average fractional concentration of the first component in the series of mixtures, and $C'_{ab}$ is the value of the cross-correlation function between a(x) and b(x).

9. A device as claimed in claim 8 wherein the spectrometer means is a near-infrared reflectance spectrometer.

10. A device as claimed in claim 7 wherein the means for spectral reconstruction cross-correlates the reference values and spectral values according to the equation:

$$C''_{ab} = \left[\frac{\sum_{x=1}^{n} [a(x) - \bar{a}][b(x) - \bar{b}]}{\sum_{x=1}^{n} [b(x) - \bar{b}]^2}\right] (1 - \bar{b}) + \bar{a} \quad (5)$$

wherein n is the number of mixtures in the series of mixtures, x is the mixture index, a(x) is the spectral value of the mixture x at the first wavelength, b(x) is the reference value of the first component in the mixture x, $\bar{a}$ is the average spectral value of all mixtures in the series of mixtures at a first wavelength, $\bar{b}$ is the average fractional concentration of the first component in the series of mixtures, and $C''_{ab}$ is the value of the cross-correlation function between a(x) and b(x).

11. A device as claimed in claim 10 wherein the spectrometer means is a near-infrared reflectance spectrometer.

12. A device as claimed in claim 7 wherein the spectrometer means is a near-infrared reflectance spectrometer.

13. A method for reconstructing the spectrum of a specific component from a series of multicomponent mixtures, each mixture capable of exhibiting a composite spectrum, the method comprising:

(a) obtaining the concentration of the specific component in each mixture in the series;

(b) measuring a composite spectral value for each mixture in the series at a plurality of wavelengths; and (c) for each of the plurality of wavelengths, cross-correlating an array comprised of the measured composite spectral value for each mixture in the series of mixtures with a correspondingly ordered array of the concentration of the specific component in each mixture in the series of mixtures to generate a reconstructed spectral value associated with the specific component.

14. The method of claim 13 wherein the step of measuring the composite spectral value for each mixture in the series comprises:

(a) selecting a plurality of wavelengths at which it is desired to have a reconstructed spectral value for the specific component; and (b) generating an array of composite spectral values at each of the selected wavelengths, each array of composite spectral values comprising the measured spectral value of each mixture at one of the selected wavelengths.

15. The method of claim 14 wherein the step of cross-correlating the array of composite spectral values for each mixture with the correspondingly ordered array of concentrations of the first component comprises calculating:

$$C_{ab}(d) = \frac{1}{n} \sum_{x=1}^{n} a(x)b(x \pm d) \quad d = 0, 1, 2 \ldots n - 1 \quad (1)$$

wherein, n is the number of mixtures in the series, x is the series index, d is the displacement from the current x index, a(x) is the measured spectral value of the xth mixture at a specific one of the selected wavelengths, b(x) is the concentration of the first component in the xth mixture, and $C_{ab}(d)$ is the value of the cross-correlation function a(x) and b(x) at the displacement d.

16. The method of claim 14 wherein the step of cross-correlating the array of composite spectral values for each mixture with the correspondingly ordered array of concentrations of the first component further comprises compensating the value of the cross-correlative function for experimental noise and interference.

17. The method of claim 16 wherin the step of compensating the value of the cross-correlation function comprises cross-correlating the array of composite spectral values for each mixture with the correspondingly ordered array of concentrations of the first component according to the calculation:

$$C'_{ab} = \frac{\sum_{x=1}^{n} [a(x) - \bar{a}][b(x) - \bar{b}]}{\sum_{x=1}^{n} [b(x) - \bar{b}]^2} \quad (4)$$

wherein, n is the number of mixtures in the series, series index, a(x) is the measured spectral value of the xth mixture at a specific one of the selected wavelengths, $\bar{a}$ is the average spectral value of all samples at the same specific one of the selected wavelengths, b(x) is the concentration of the first component in the xth mixture, $\bar{b}$ is the average fractional concentration of a given component, the denominator in the equation is the variance of b(x), and $C'_{ab}$ is the compensated and normalized value of the cross-correlation function a(x) and b(x).

18. The method of claim 17 wherein the step of cross-correlating the array of composite spectral values for each mixture with the correspondingly ordered array of concentrations of the first component further comprises compensating for mixtures in which the fractional concentration of another component in the mixture influences the concentration of the specific component for which the spectral reconstruction is desired.

19. The method of claim 1 or 13 further comprising repeating the reconstruction of spectra for additional components of the mixtures.

* * * * *